(12) United States Patent
Cetrangelo

(10) Patent No.: US 7,578,884 B1
(45) Date of Patent: Aug. 25, 2009

(54) DEVICE FOR CLEANING DENTAL INSTRUMENTS

(76) Inventor: Regina A. Cetrangelo, 1 Johnson Ct., Centereach, NY (US) 11720

( * ) Notice: Subject to any disclaimer, the term of this patent is extended or adjusted under 35 U.S.C. 154(b) by 1394 days.

(21) Appl. No.: 10/656,953

(22) Filed: Sep. 8, 2003

Related U.S. Application Data

(63) Continuation-in-part of application No. 10/043,331, filed on Jan. 14, 2002, now abandoned.

(60) Provisional application No. 60/330,402, filed on Oct. 18, 2001.

(51) Int. Cl.
*B08B 7/00* (2006.01)
(52) U.S. Cl. .............................. 134/6; 15/97.1; 15/210.1
(58) Field of Classification Search ...................... 134/6; 15/210.1, 244.1, 97.1
See application file for complete search history.

(56) References Cited

U.S. PATENT DOCUMENTS

| | | | | |
|---|---|---|---|---|
| 4,362,241 A | * | 12/1982 | Williams | 206/210 |
| 4,530,726 A | * | 7/1985 | Montiel | 134/6 |
| 5,471,706 A | * | 12/1995 | Wallock et al. | 15/302 |
| 5,639,310 A | * | 6/1997 | Giampaolo, Jr. | 134/6 |
| 5,704,088 A | * | 1/1998 | Cerroni | 15/160 |
| 5,997,655 A | * | 12/1999 | Schang | 134/6 |
| 2003/0029474 A1 | * | 2/2003 | Gibbs et al. | 134/1 |

* cited by examiner

*Primary Examiner*—Michael Kornakov
*Assistant Examiner*—Eric Golightly
(74) *Attorney, Agent, or Firm*—Richard L. Huff

(57) ABSTRACT

A device made of flexible material for cleaning sharp-tipped dental instruments. The device contains a) a finger rest, b) a stem, and c) an open container having a textured exterior surface, an interior surface, and a top. The exterior surface may have a girth near the top. The interior surface may be rough and contain a plurality of prongs and ribs. The top has a protective rim. For use, gauze is put into the container and the gauze is contacted with the sharp tip of the dental instrument. Pressure is applied to the container to help create a firm contact between the gauze and the instrument. The prongs help to keep the gauze in place while the instrument is being removed. The use of this device helps prevent puncture wounds or cuts caused by the dental instrument and the accompanying possibility of infection.

10 Claims, 3 Drawing Sheets

DEVICE FOR CLEANING DENTAL INSTRUMENTS

CROSS-REFERENCE TO RELATED APPLICATIONS

This application is a continuation-in-part of application Ser. No. 10/043,331 filed Jan. 14, 2002, now abandoned, which claims the benefit of the filing date of U.S. provisional application Ser. No. 60/330,402 filed Oct. 18, 2001.

BACKGROUND OF THE INVENTION

1. Field of the Invention

This invention relates to a protective device to help to avoid wound punctures while using sharp dental or medical instruments.

2. Description of the Related Art

In the practice of dentistry, it is necessary in most procedures to manipulate various kinds of instruments in the patient's mouth. One notable example is the cleaning of the teeth which should be periodically performed to remove plaque, tartar and calculus from the teeth. If left undisturbed, this material can lead to the formation of gingivitis and periodontitis.

As is commonly known, the cleaning procedure involves the scaling or scraping away of such matter that has adhered to the surface of the teeth, especially in the vicinity of the gum line and in intra-proximal regions. For this purpose, a dental hygienic technician or a dentist utilizes scalers, scrapers, or picks shaped at their operative ends in various configurations designed to achieve the necessary scraping and cleaning action.

As the cleaning proceeds, these scalers or picks inevitably collect at their operative ends the plaque or other debris removed from the teeth. Consequently, the end of the instrument must be freed of this debris at frequent intervals so that further cleaning can proceed without interference by the accumulated debris on the cleaning action of the instrument or obstruction of the field of view of the practitioner of the site being cleaned.

Typical dental chairs are equipped with instrument trays mounted on articulated and pivotable arms permitting the tray to be positioned at a location relative to the operator and patient affording convenient access to various instruments and the like placed thereon for use in cleaning. For ridding the end of the cleaning instrument of the accumulated debris, there is ordinarily placed loosely on this tray a paper tissue, gauze pad, or other absorbent wiping material with which the practitioner can wipe the instrument end free of adherent matter. In the step of cleaning the instrument, the instrument comes in close proximity to the practitioner's hand, which is protected only by a plastic glove. This introduces a significant risk of the occurrence of the penetration of the skin of the hand holding the wiping material by the sharp instrument.

Since the advent of the wide-spread dissemination of HIV and hepatitis viruses, much attention in the health care professions has been given to the avoidance of the penetration of the skin by sharp points of hypodermic needles and the like used in the administration of medicaments to patients either at the time of administration or subsequently in the disposal of the needles.

It is now common knowledge that such needle or instrument sticks can result in the transmission to the practitioner of serious diseases carried by the patients, including AIDS and hepatitis, the viruses of which are known to be present in oral mucous as well as in blood serum and other bodily fluids. Thus, microorganisms from dental patients can be borne by debris, mucous, and blood collected on the ends of cleaning instruments and transmitted to a practitioner by an accidental pricking or scratching of the skin with potentially serious consequences. Any measure for reducing the possibility of casual instrument sticks in the dental field is highly desirable.

The same considerations with attendant risks obviously apply to other dental procedures including endodontic and periodontal procedures, filling of teeth and the like employing files, reamers, probes, drills, and other instruments which become coated with mucous or blood during the procedure and likewise require wiping or cleaning from time to time.

In view of these risks, in 1993 the Centers for Disease Control published guidelines for controlling infections in hospitals. One section, entitled "Blood and Body Fluid Precautions", recommended that certain precautions be taken in handling the blood and body fluids of patients who were known or suspected of being infected with blood-borne pathogens. Special precautions were recommended to be followed with such patients. The Federal Register of Dec. 6, 1991, in "Blood-Borne Pathogen Standards" under Methods of Compliance, stated in pertinent parts that universal precautions shall be observed to prevent contact with blood and other potentially infectious materials under circumstances in which differentiation between body fluid types is difficult or impossible, all body fluid shall be considered potentially infectious material. Under Engineering and Work Practice Control, it notes that engineering and work practice controls shall be used to eliminate or minimize employee exposure or when occupational exposure remains after institution of these controls, personal protection equipment shall also be used, such as gloves, masks, etc.

The prior art contains teachings of devices which are designed to minimize the risk of accidental contamination with oral debris by providing methods of cleaning sharp dental instruments by means other than gauze held by a gloved hand.

U.S. Pat. No. 4,439,884 discloses a round, cup-like container having an array of bristles around the inside surface of the container pointing toward the center of the container. A dental instrument is inserted through the top of the container and the bristles brush against it to clean it. The device is maintained in an upright position, the bottom may contain liquid, and the device may be taken apart to be cleaned.

U.S. Pat. Nos. 5,308,406 and 5,471,706 disclose devices for cleaning dental instruments. The first of these references discloses a cylindrical container with bristles covering the inner surface and extending toward the center. The device stands on its own, may be taken apart for cleaning, and is deep enough to hold a pool of liquid in the bottom. The device has a self-sealing entrance made of flexible material to contain the liquid. Additionally, there is a protective collar around the opening. The second of the above patents discloses the same container and additionally discloses a means for withdrawing liquid from the container by attaching the device to a source of suction.

U.S. Pat. No. 5,477,581 discloses a device for cleaning dental instruments which contains a strip having adhesive material on both the top and the bottom. The bottom of the strip attaches to a dental tray and the top attaches to two adjacent rolls of rough absorbent material. The tip of the dental instrument is placed between the two rolls for cleaning.

U.S. Pat. No. 5,704,088 discloses a device for cleaning dental instruments. The device may be held in one hand while the instrument is held in the other. The device is made up of a flexible sealed chamber having a hinge, a bottom and a top. The bottom and the top have brush elements. The portion of the instrument to be cleaned is placed between the brush elements and the flexible top and bottom are compressed to apply pressure to the brush elements.

U.S. Pat. No. 5,778,480 discloses a device for cleaning dental instruments. The device contains a saucer which is attached through a clamp to the dental tray. A cleaning head is carried on top of the saucer, and the dental instrument is cleaned by rubbing the instrument against the cleaning head.

U.S. Pat. No. 6,257,888 discloses a device for cleaning dental instruments. The device is made up of a small container which adhesively attaches to the back of a plastic glove. The container carries two pieces of a flexible wiping medium such as cellular foam or quilted dental padding. The tip of the instrument is placed between the two pieces for cleaning.

U.S. Pat. No. 6,280,529 shows a laminated pad of gauze or sponge for cleaning dental instruments. The pad may be attached to the back of a glove by adhesive or a strap and the instrument may be cleaned by wiping it over the pad.

The above devices, while being useful, contain inherent disadvantages. The stand-alone devices which contain bristles are complex devices which may be seen to be not worth the cost in order to replace a nearly cost-free procedure. Also, in the absence of pressure being applied to the bristles, the instruments may not be cleaned to the extent desired. The devices which attach to gloves become inconvenient when they must be transferred every time gloves are changed. In each of the discussed devices, the practitioner has the choice of changing the device or at least the cleaning surface of the device or subjecting a dental instrument being used in one patient to the debris removed from previous patients. The first option becomes expensive while the second option is so unsanitary as to not be a viable option.

In spite of the multiplicity of devices for cleaning dental instruments which has been made available to the dental profession, the method of choice remains picking up a piece of gauze and wiping the tip of the instrument with the gauze while applying pressure. While being simple and inexpensive, this method carries with it the possibility of punctures and cuts which can introduce unwanted pathogens into the bloodstream of the practitioner.

SUMMARY OF THE INVENTION

The purpose of the present invention is to overcome the inherent disadvantages of the prior art and to provide a safe, inexpensive, sanitary, and simple device for cleaning dental instruments.

The device of the present invention is an open container into which dental gauze may be placed. The device is made up of a finger rest, a stem, and an open container having a girth near the open end and a protective rim at the open end. Protruding prongs on the inner surface of the open container aid in keeping the gauze in place. The device is made of a flexible material which allows pressure to be put on the gauze for assuring firm contact between the gauze and the instrument.

In use, the device may be held in one hand and the dental instrument in the other. The sharp, pointed tip of the dental instrument is placed inside the open container in contact with the gauze. Pressure is applied to the container to assure firm contact and good cleaning ability. The tip of the instrument is wiped by the gauze, following which the instrument is removed.

DETAILED DESCRIPTION OF THE INVENTION

Figure 1:
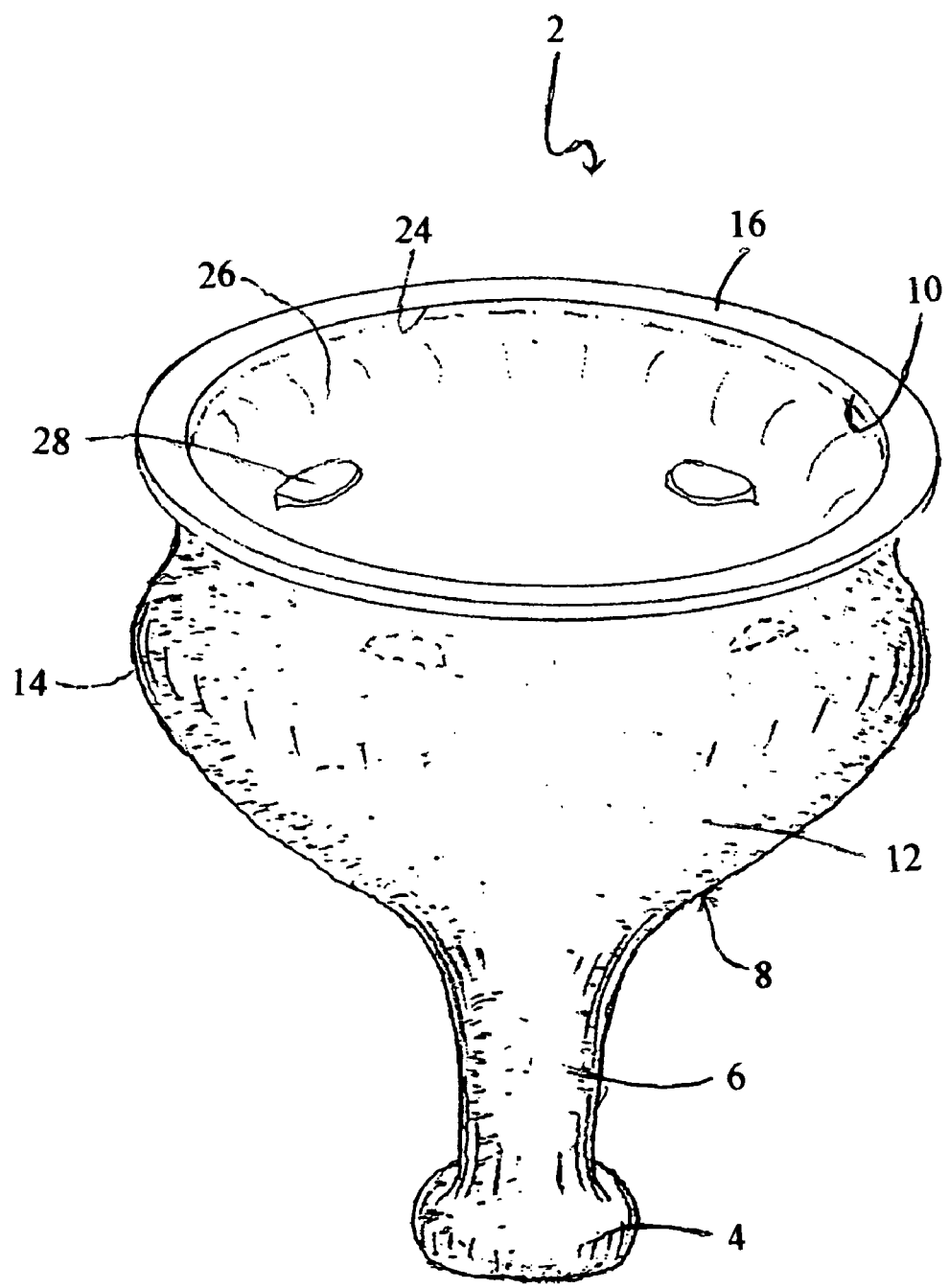
FIG. 1 is an elevational perspective view of the device of one embodiment of the invention.

The invention will now be described with reference to the above drawing, like reference numerals referring to like parts throughout the description.

Referring to FIGS. 1-6, the device 2 of the present invention is made of flexible material such as silicone, flexible plastic, or rubber and contains a finger rest 4 which serves to maintain the practitioner's fingers on the device 2 and to prevent the practitioner from losing his or her grip on the device 2.

The stem 6 of the device 2 is used as a handle and is contacted by one or two fingers.

Figure 2:
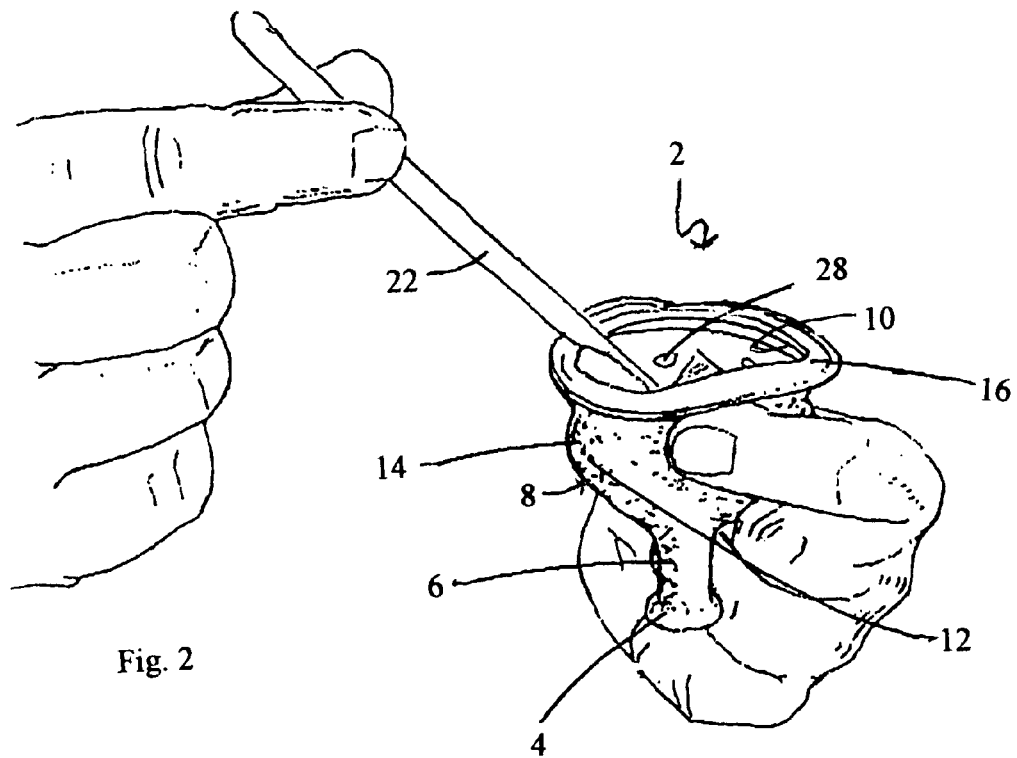
FIG. 2 is an elevational perspective view of the device of FIG. 1 having finger pressure applied to it and a dental instrument being cleaned.
Figure 3:
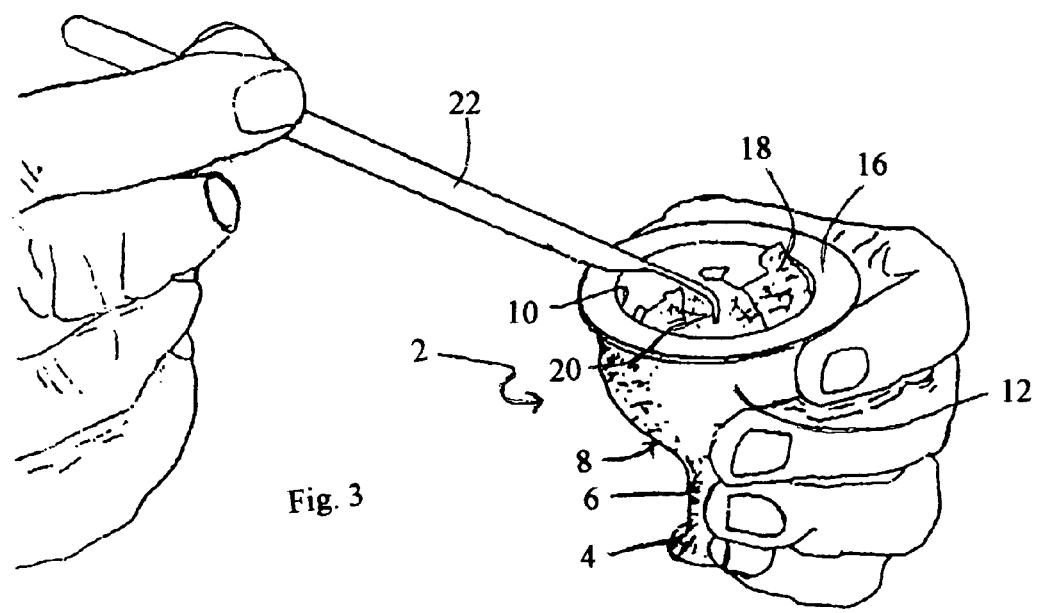
FIG. 3 is an elevational perspective view of the device showing a dental instrument being removed from the open container following cleaning.
Figure 6:
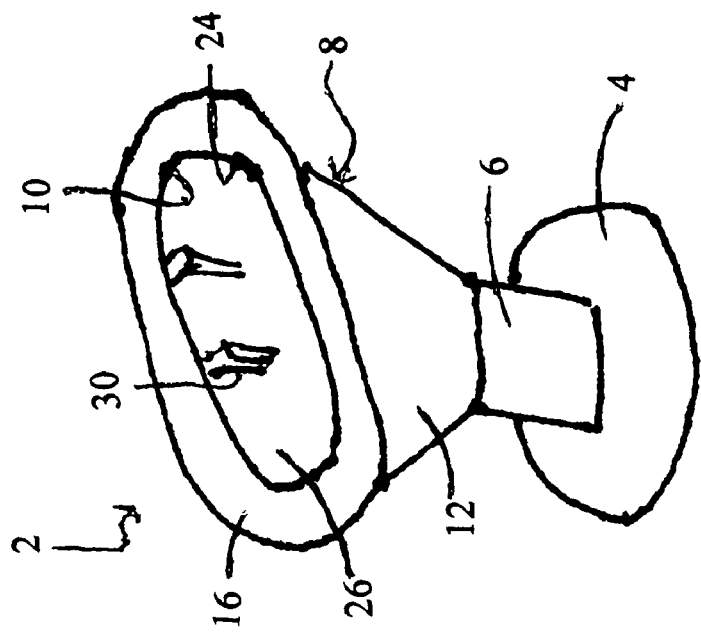
FIG. 6 is an elevational perspective view of the device of another embodiment of the invention.
Figure 5:
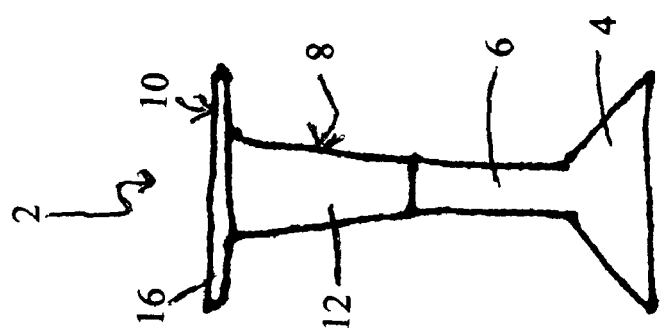
FIG. 5 is an elevational end view of the device shown in FIG. 4.
Figure 4:
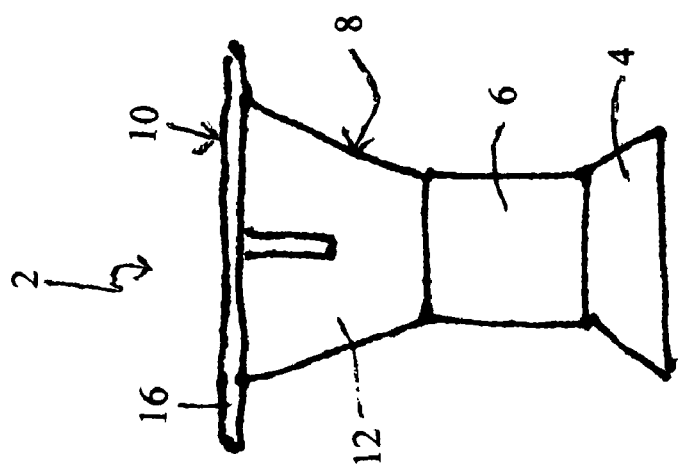
FIG. 4 is an elevational side view of the device shown in FIG. 4.

The device may have a circular cross-section as shown in FIGS. 1-3 or an oblong cross-section as shown in FIGS. 4-6. The container 8 portion of the device 2 is contoured in shape and contains an open top 10.

The exterior surface 12 is textured to assist in the gripping action of a gloved hand, thus keeping the fingers from sliding. An exterior feature of the container 8 of the first embodiment is a girth 14 located near the top 10 of the container 8. The wideness of the girth 14 provides an additional area for the fingers to grasp the device 2. An exterior feature common to both embodiments is a protective rim 16 at the top 10 of the container 8.

In operation, pressure is applied to the container 8 to squeeze the gauze 18 and so to assure good contact between the gauze 18 and the tip 20 of the dental instrument 22.

The protective rim 16 lies at the top 10 of the container 8 and encircles the opening 24. The protective rim 16 provides an extended area assuring that if the instrument 22 somehow misses the opening 24 of the device 2, it will not hit the hand of the practitioner, but will be stopped by the rim 16.

The interior surface 26 of the open container 8 contains a plurality of prongs 28 which are extensions of the interior surface 26. The purpose of the prongs 28 is to assure that the folded dental gauze 18 held in the open container 8 does not fall out or escape when the dental instrument 22 is removed from the container 8.

The interior may be lined with reinforcing ribs 30 to further aid in keeping the gauze 18 in place. These ribs 30 may act as a surface which would grasp debris from the dental instrument 22.

The open container 8 may be constructed of two parts, a hard exterior plastic and a rough, softer interior plastic. This arrangement increases the beneficial properties of the device 2. The hard exterior surface is not penetrated by a sharp dental instrument 22 from the inside of the device 2. The roughness of the interior layer helps to keep the gauze 18 in place.

In use, the device 2 may be held in one hand by placing one or two fingers on the stem 6 and the remaining fingers and thumb about the exterior surface 12 of the container 8. The dental instrument 22 is held in the other hand. The sharp, pointed tip 20 of the dental instrument 22 is placed inside the open container 8 and is put in contact with the gauze 18. Pressure is applied to the container 8 to assure firm contact between the instrument 22 and the gauze 18 and good cleaning ability. The tip 20 of the instrument 22 is wiped by the gauze 18, following which the instrument 22 is removed from the open container 8. During the step of applying pressure, the prongs 28 enter the gauze 18 and tend to keep the gauze 18 in place while the instrument 22 is being removed.

Although the invention has been described and illustrated in detail, it is to be clearly understood that the same is by way of illustration and example, and is not to be taken by way of limitation. The spirit and scope of the present invention are to be limited only by the terms of the appended claims.

I claim:

1. A device for use in the cleaning of dental instruments comprising:
   a) a finger rest,
   b) a stem,
   c) an open container having an exterior surface, an interior surface, and a top, said exterior surface having a girth near the top, said interior surface containing a plurality of prongs, and said top having a protective rim.

2. The device of claim 1, wherein the exterior surface is textured.

3. The device of claim 1, wherein a cross-section of the device is round.

4. The device of claim 1, wherein the container contains gauze.

5. A device for use in the cleaning of dental instruments comprising:
   a) a finger rest,
   b) a stem,
   c) an open container having an exterior surface, an interior surface, and a top, said interior surface containing a plurality of prongs, and said top having a protective rim.

6. The device of claim 5, wherein the container contains gauze.

7. The device of claim 5, wherein the device is made of flexible material.

8. The device of claim 5, wherein the exterior surface of the open container is made of hard plastic and the interior surface of the open container is made of soft plastic.

9. A method of cleaning a dental instrument having a pointed tip which comprises:
   a) holding the device of claim 4 in one hand,
   b) holding the dental instrument in the other hand,
   c) placing the pointed tip of the dental instrument inside the open container,
   d) putting the pointed tip of the dental instrument in contact with the gauze,
   e) applying pressure to the container to assure firm contact between the instrument and the gauze,
   f) wiping the tip of the instrument on the gauze, and
   g) removing the instrument from the open container.

10. A method of cleaning a dental instrument having a pointed tip which comprises:
   a) holding the device of claim 6 in one hand,
   b) holding the dental instrument in the other hand,
   c) placing the pointed tip of the dental instrument inside the open container,
   d) putting the pointed tip of the dental instrument in contact with the gauze,
   e) applying pressure to the container to assure firm contact between the instrument and the gauze,
   f) wiping the tip of the instrument on the gauze, and
   g) removing the instrument from the open container.

* * * * *